(12) United States Patent
Abrecht et al.

(10) Patent No.: US 8,420,818 B2
(45) Date of Patent: Apr. 16, 2013

(54) PROCESS FOR THE PREPARATION OF PYRIDO[2,1-A] ISOQUINOLINE DERIVATIVES

(75) Inventors: Stefan Abrecht, Duggingen (CH); Jean-Michel Adam, Rosenau (FR); Alec Fettes, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/274,523

(22) Filed: Oct. 17, 2011

(65) Prior Publication Data

US 2012/0035368 A1  Feb. 9, 2012

Related U.S. Application Data

(63) Continuation of application No. 12/326,976, filed on Dec. 3, 2008, now abandoned.

(30) Foreign Application Priority Data

Dec. 19, 2007  (EP) .................................... 07150174

(51) Int. Cl.
*C07D 455/06* (2006.01)
(52) U.S. Cl.
USPC ............................................ 546/95; 546/146
(58) Field of Classification Search .................... 546/95, 546/146
See application file for complete search history.

(56) References Cited

FOREIGN PATENT DOCUMENTS

| WO | 2005000848 | 1/2005 |
|---|---|---|
| WO | 2006125728 | 11/2006 |
| WO | 2007/017423 | 2/2007 |
| WO | 2007/128801 | 11/2007 |

OTHER PUBLICATIONS

International Search Report (PCT/EP2008/067136 Mar. 31, 2009).
(Translation of Japanese Office Action in Corresponding Jap App 2010538572 Dec. 4, 2012).

*Primary Examiner* — David K O Dell
(74) *Attorney, Agent, or Firm* — George W. Johnston; Dennis P. Tramaloni; Gene J. Yao

(57) ABSTRACT

The present invention relates to a novel process for the preparation of pyrido[2,1-a]isoquinoline derivatives of the formula

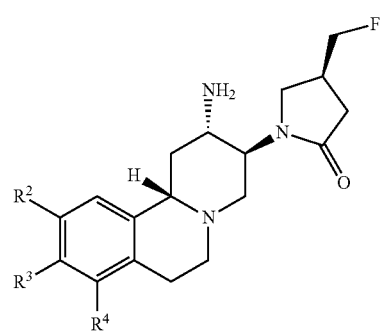

wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group consisting of lower alkoxycarbonyl, aryl and heterocyclyl, and the pharmaceutically acceptable salts thereof. The pyrido[2,1-a]isoquinoline derivatives of the formula I are useful for the treatment and/or prophylaxis of diseases which are associated with DPP IV.

16 Claims, No Drawings

PROCESS FOR THE PREPARATION OF PYRIDO[2,1-A] ISOQUINOLINE DERIVATIVES

PRIORITY TO RELATED APPLICATION(S)

This application is a continuation of U.S. application Ser. No. 12/326,976, filed Dec. 3, 2008, now Pending, which claims the benefit of European Application No. 07150174.6, filed Dec. 19, 2007. The entire contents of the above-identified applications are hereby incorporated by reference.

BACKGROUND OF THE INVENTION

A major task in the synthesis of the compounds of formula I is the introduction of the chiral centers in the pyrido[2,1-a] isoquinoline moiety, which in the synthesis according to the PCT Int. Appl. WO 2005/000848 involves late stage enantiomer separation by chiral HPLC. Such a process is however difficult to manage on technical scale. The problem to be solved was therefore to find a suitable process alternative which allows obtaining the desired optical isomer in an earlier stage of the process, affords a higher yield and which can be conducted on technical scale.

All documents cited to or relied upon herein is expressly incorporated herein by reference.

SUMMARY OF THE INVENTION

The present invention relates to a process of the preparation of pyrido[2,1-a]isoquinoline derivatives of the formula

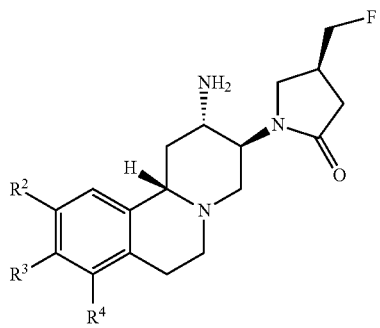

wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group consisting of lower alkoxycarbonyl, aryl and heterocyclyl, and the pharmaceutically acceptable salts thereof, which are useful for the treatment and/or prophylaxis of diseases which are associated with DPP IV.

The present invention relates particularly to a process of the preparation of a pyrido[2,1-a]isoquinoline derivative of the formula

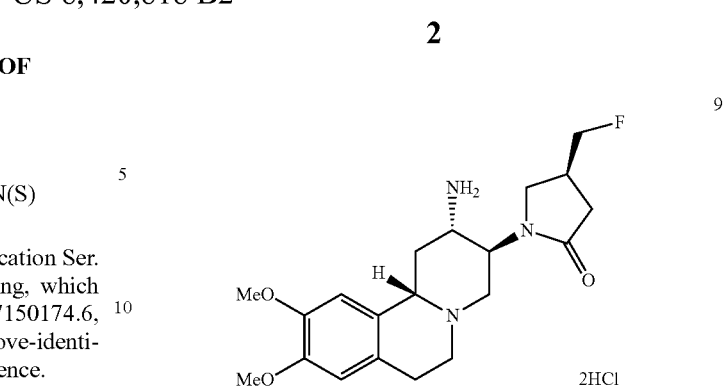

Pyrido[2,1-a]isoquinoline derivatives of the formula I are disclosed in PCT International Patent Appl. WO 2005/000848.

DETAILED DESCRIPTION OF THE INVENTION

Provided is a process for the preparation of pyrido[2,1-a] isoquinoline derivatives of the formula

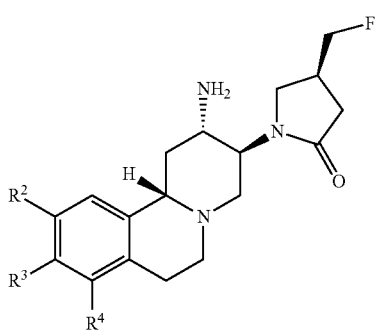

wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl, and of pharmaceutically acceptable salts thereof, comprises one or more of the following steps a) ring opening of (S)-4-fluoromethyl-dihydro-furan-2-one of the formula

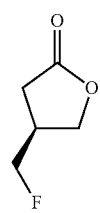

and subsequent esterification to provide the (R)-4-bromo-3-fluoromethyl-butyric acid ester of the formula

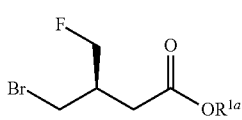

wherein $R^{1a}$ is lower alkyl;

b) converting the (R)-4-bromo-3-fluoromethyl-butyric acid ester of the formula (2) with an N-protected glycine alkylester into a N-protected-(S)-4-(alkoxycarbonylmethyl-amino)-3-fluoromethyl-butyric acid ester of formula

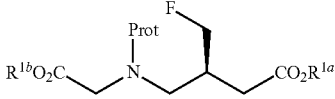

wherein $R^{1a}$ and $R^{1b}$ are lower alkyl and Prot is an amino protecting group;

c) deprotecting the N-protected —(S)-4-(alkoxycarbonylmethyl-amino)-3-fluoromethyl-butyric acid ester of formula (3) and subsequent ring closure to form the ((S)-4-fluoromethyl-2-oxo-pyrrolidin-1-yl)-acetic acid ester of formula

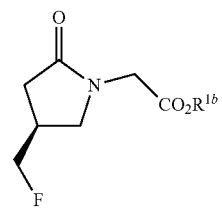

wherein $R^{1b}$ is lower alkyl;

d) converting the ((S)-4-fluoromethyl-2-oxo-pyrrolidin-1-yl)-acetic acid ester of formula (4) into the ((S)-4-fluoromethyl-2-oxo-pyrrolidin-1-yl)-3-oxo-butyric acid ester of formula

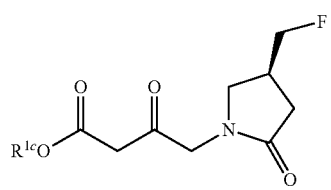

wherein $R^{1c}$ is a protecting group or a salt thereof;

e) transforming the ((S)-4-fluoromethyl-2-oxo-pyrrolidin-1-yl)-3-oxo-butyric acid ester of formula (5a) into the ((S)-4-fluoromethyl-2-oxo-pyrrolidin-1-yl)-3-oxo-butyric acid of formula

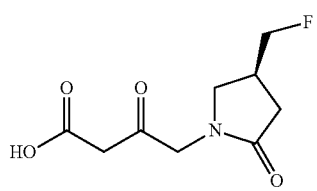

or a salt thereof;

coupling the ((S)-4-fluoromethyl-2-oxo-pyrrolidin-1-yl)-3-oxo-butyric acid of formula (5b) with an isoquinoline derivative of formula

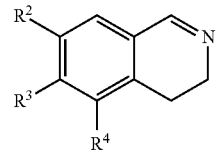

or a salt thereof, wherein $R^2$, $R^3$ and $R^4$ are as above, to form a compound of formula

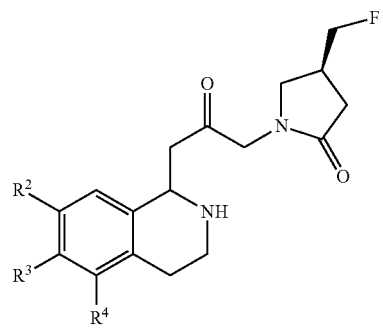

wherein $R^2$, $R^3$ and $R^4$ are as above, or a salt thereof, subsequently ring closing the compound of formula (7a) with formaldehyde to form the (3S,11bS)-3-((S)-4-fluoromethyl-2-oxo-pyrrolidin-1-yl)-1,3,4,6,7,11b-hexahydro-pyrido[2,1-a]isoquinolin-2-one derivative of formula

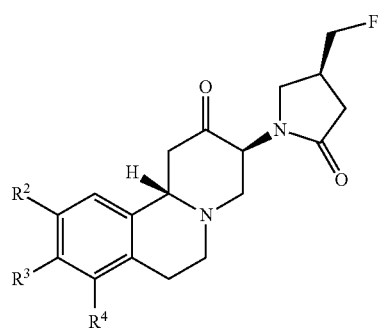

wherein $R^2$, $R^3$ and $R^4$ are as above, or a salt thereof;

g) transforming the (3S,11bS)-3-((S)-4-fluoromethyl-2-oxo-pyrrolidin-1-yl)-1,3,4,6,7,11b-hexahydro-pyrido[2,1-a] isoquinolin-2-one derivative of formula (7b) into the (S)-1-((2S,3S,11bS)-2-N-protected-amino-1,3,4,6,7,11b-hexahydro-2H-pyrido[2,1-a]isoquinolin-3-yl)-4-fluoromethyl-pyrrolidin-2-one of formula

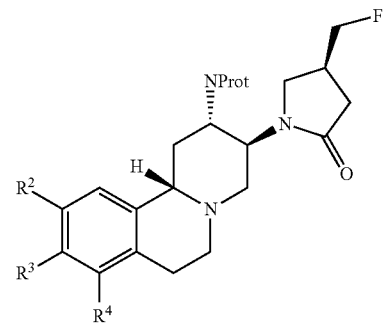

wherein $R^2$, $R^3$ and $R^4$ and Prot are as above, or a salt thereof;

h) removing the protecting group Prot in the (S)-1-((2S,3S,11bS)-2-N-protected-amino-1,3,4,6,7,11b-hexahydro-2H-pyrido[2,1-a]isoquinolin-3-yl)-4-fluoromethyl-pyrrolidin-2-one of formula (8).

Unless otherwise indicated, the following definitions are set forth to illustrate and define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, with fluorine, bromine and chlorine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

The term "halogenated lower alkyl" refers to a lower alkyl group as defined above wherein at least one of the hydrogens of the lower alkyl group is replaced by a halogen atom, preferably fluoro or chloro. Among the preferred halogenated lower alkyl groups are trifluoromethyl, difluoromethyl, fluoromethyl and chloromethyl.

The term "alkenyl" as used herein denotes an unsubstituted or substituted hydrocarbon chain radical having from 2 to 6 carbon atoms, preferably from 2 to 4 carbon atoms, and having one or two olefinic double bonds, preferably one olefinic double bond. Examples are vinyl, 1-propenyl, 2-propenyl(allyl) or 2-butenyl(crotyl).

The term "alkoxy" refers to the group R'—O—, wherein R' is alkyl. The term "lower-alkoxy" refers to the group R'—O—, wherein R' is a lower alkyl group as defined above. Examples of lower alkoxy groups are e.g. methoxy, ethoxy, propoxy, isopropoxy, butoxy, isobutoxy and hexyloxy, with methoxy being especially preferred.

The term "lower alkoxycarbonyl" refers to the group R'—O—C(O)—, wherein R' is a lower alkyl group as defined above.

The term "aryl" refers to an aromatic monovalent mono- or polycarbocyclic radical, such as phenyl or naphthyl, preferably phenyl, which may optionally be mono-, di- or tri-substituted, independently, by lower alkyl, lower alkoxy, halo, cyano, azido, amino, di-lower alkyl amino or hydroxy.

The term "cycloalkyl" refers to a monovalent carbocyclic radical of three to six, preferably three to five carbon atoms. This term is further exemplified by radicals such as cyclopropyl, cyclobutyl, cyclopentyl and cyclohexyl, with cyclopropyl and cyclobutyl being preferred. Such cycloalkyl residues may optionally be mono-, di- or tri-substituted, independently, by lower alkyl or by halogen.

The term "heterocyclyl" refers to a 5- or 6-membered aromatic or saturated N-heterocyclic residue, which may optionally contain a further nitrogen or oxygen atom, such as imidazolyl, pyrazolyl, thiazolyl, pyridyl, pyrimidyl, morpholino, piperazino, piperidino or pyrrolidino, preferably pyridyl, thiazolyl or morpholino. Such heterocyclic rings may optionally be mono-, di- or tri-substituted, independently, by lower alkyl, lower alkoxy, halo, cyano, azido, amino, di-lower alkyl amino or hydroxy. Preferable substituent is lower alkyl, with methyl being preferred.

The term "salt" refers to salts that are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

Step a)

Step a) requires the ring opening of (S)-4-fluoromethyl-dihydro-furan-2-one of the formula (1) and subsequent esterification to provide the (R)-4-bromo-3-fluoromethyl-butyric acid ester of the formula (2).

The ring opening reaction usually takes place with hydrobromic acid, suitably with an acetic acid solution of hydrobromic acid at a reaction temperature of 20° C. to 100° C., preferably of 40° C. to 80° C.

For the subsequent esterification a lower alcohol, preferably methanol or ethanol, more preferably methanol is added to the reaction mixture. The reaction temperature is not critical, but usually it is kept below 40° C.

Alternatively the ring opening and the esterification can be effected directly by reacting the (S)-4-fluoromethyl-dihydro-furan-2-one with a hydrobromic acid solution in the lower alcohol at the conditions as outlined above.

Upon completion of the reaction the (R)-4-bromo-3-fluoromethyl-butyric acid ester of the formula (2) can be isolated applying aqueous work up methods known to the skilled in the art. Further purification of the product can be achieved by distillation.

Step b)

Step b) requires converting the (R)-4-bromo-3-fluoromethyl-butyric acid ester of the formula (2) with an N-protected glycine alkylester into a N-protected —(S)-4-(alkoxycarbonylmethyl-amino)-3-fluoromethyl-butyric acid ester of formula (3).

Preferred (R)-4-bromo-3-fluoromethyl-butyric acid ester of formula (2) is the corresponding methylester.

Suitable N-protected glycine alkylester is a N-protected glycine lower alkyl ester, preferably the methyl- or ethylester.

The N-protecting group "Prot" may refer to any substituents conventionally used to hinder the reactivity of the amino group. Suitable amino protecting groups are described in Green T., "Protective Groups in Organic Synthesis", Chapter 7, John Wiley and Sons, Inc., 1991, 309-385. The benzyl group was found to be the preferred N-protecting group "Prot".

Most preferred N-protected glycine alkylester therefore is the N-benzyl glycine ethylester.

The reaction is usually performed in a suitable polar aprotic solvent such as in acetonitrile, tetrahydrofuran, dimethoxyethane, dioxane or triethyalmine, preferably in acetonitrile at a reaction temperature of 60° C. to the reflux temperature of the solvent, usually at the reflux temperature of the solvent.

The product of step b), preferably the (S)-4-(benzyl-ethoxycarbonylmethyl-amino)-3-fluoromethyl-butyric acid methyl ester can be isolated applying methods known to the skilled in the art for example by removing the solvent. Purification can be achieved by filtering the residue over silica gel using a suitable organic solvent or organic solvent mixture as eluent, for example a mixture of ethylacetate and heptane.

Step c)

Step c) requires the deprotection of the N-protected-(S)-4-(alkoxycarbonylmethyl-amino)-3-fluoromethyl-butyric acid ester of formula (3) and subsequent ring closure to form the ((S)-4-fluoromethyl-2-oxo-pyrrolidin-1-yl)-acetic acid ester of formula (4).

In a first step the N-protecting group "Prot" is removed by way of a hydrogenolysis applying conditions which are known to the skilled in the art (see e.g. "Hydrogenolysis of Benzyl Groups Attached to Oxygen, Nitrogen, or Sulfur." Org. React. (N.Y.) 7: 263).

For the preferred debenzylation the hydrogenolysis can as a rule be performed under a hydrogen atmosphere of 1 bar to 10 bar in the presence of a common hydrogenation catalyst such as palladium or platinum on an inert support like charcoal and in a lower alcohol, preferably ethanol as solvent.

The reaction temperature is expediently selected between 0° C. and 60° C., preferably 10° C. to 30° C.

Ring closing can already be observed in the course of the hydrogenolysis. Completion of the ring closing can be achieved by raising the reaction temperature, preferably to reflux temperature of the solvent. The catalyst can be filtered off prior to the temperature increase.

The product of step c), preferably the ((S)-4-fluoromethyl-2-oxo-pyrrolidin-1-yl)-acetic acid ethyl ester can be isolated from the reaction mixture by removing the solvent and, if desired by subsequent distillation of the residue.

The ((S)-4-fluoromethyl-2-oxo-pyrrolidin-1-yl)-acetic acid ester of formula

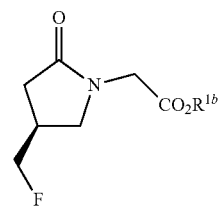

4 wherein $R^{1b}$ is lower alkyl, particularly the ((S)-4-fluoromethyl-2-oxo-pyrrolidin-1-yl)-acetic acid ethyl ester is novel and thus represents a further embodiment of the invention.

Step d)

Step d) requires the conversion of the ((S)-4-fluoromethyl-2-oxo-pyrrolidin-1-yl)-acetic acid ester of formula (4) into the ((S)-4-fluoromethyl-2-oxo-pyrrolidin-1-yl)-3-oxo-butyric acid ester of formula (5a).

Initially the acetic acid ester of the formula

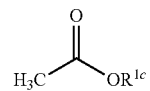

wherein $R^{1c}$ is a protecting group is deprotonated in the presence of a non nucleophilic strong organic base, such as with LDA=lithium diisopropylamide, LiHMDS=lithium hexamethyldisilazide, KHMDS=potassium hexamethyldisilazide, NaHMDS=sodium hexamethyldisilazide or LiTMP=lithium 2,2,6,6-tetramethylpiperidide at a temperature of 0° C. to −100° C., preferably 0° C. to −40° C. in the presence of suitable inert organic solvent, for example in tetrahydrofuran.

Suitable protecting group $R^{1c}$ is benzyl or 1-phenyl ethyl, preferably benzyl. Preferably benzyl acetate is used.

To the in situ formed enolate the ((S)-4-fluoromethyl-2-oxo-pyrrolidin-1-yl)-acetic acid ester of formula (4) can then be added at a temperature of −50° C. to −100° C., preferably −60° C. to −80° C. in the presence of the same solvent as used for the enolate formation.

Upon completion of the reaction the ((S)-4-fluoromethyl-2-oxo-pyrrolidin-1-yl)-3-oxo-butyric acid ester of formula (5a), preferably the ((S)-4-fluoromethyl-2-oxo-pyrrolidin-1-yl)-3-oxo-butyric acid benzyl ester can be isolated applying aqueous work up methods known to the skilled in the art. Purification of the product can be achieved by filtration over silica gel using a suitable organic solvent or organic solvent mixture as eluent, for example a mixture of ethylacetate and heptane.

The ((S)-4-fluoromethyl-2-oxo-pyrrolidin-1-yl)-3-oxo-butyric acid esters of formula

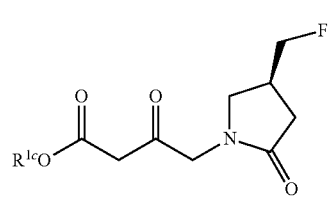

5a wherein $R^{1c}$ is a protecting group, particularly the ((S)-4-fluoromethyl-2-oxo-pyrrolidin-1-yl)-3-oxo-butyric acid benzyl ester, or a salt thereof, are novel compounds and thus represent a further embodiment of the invention.

β-Ketoesters show keto-enol tautomerism and thus the (S)-4-fluoromethyl-2-oxo-pyrrolidin-1-yl)-3-oxo-butyric acid ester can also exist in its enol form of the formula

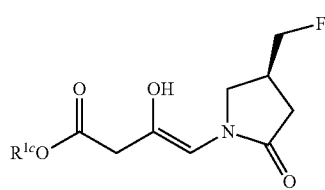

5a'

Step e)

Step e) requires the transformation of the ((S)-4-fluoromethyl-2-oxo-pyrrolidin-1-yl)-3-oxo-butyric acid ester of formula (5a) into the ((S)-4-fluoromethyl-2-oxo-pyrrolidin-1-yl)-3-oxo-butyric acid of formula (5b).

The formation of the acid as a rule consists of a hydrogeolysis which can be performed applying methods known to the skilled in the art (see e.g. W. H. Hartung, R. Smirnoff (1953). "Hydrogenolysis of Benzyl Groups Attached to Oxygen, Nitrogen, or Sulfur." Org. React. (N.Y.) 7: 263).

Usually the reaction is performed under a hydrogen atmosphere of 1 bar to 10 bar in the presence of a common hydrogenation catalyst such as palladium or platinum on an inert support like charcoal and in a lower alcohol, preferably ethanol as solvent.

The reaction temperature is expediently selected between 0° C. and 60° C., preferably 0° C. to 30° C.

The resulting ((S)-4-fluoromethyl-2-oxo-pyrrolidin-1-yl)-3-oxo-butyric acid of formula (5b) can be isolated from the reaction mixture by filtering off of the catalyst and after removal of the solvent.

However, it is preferred not to isolate the ((S)-4-fluoromethyl-2-oxo-pyrrolidin-1-yl)-3-oxo-butyric acid of formula (5b), but to use the filtrate (after removal of the catalyst) for the subsequent step f).

The ((S)-4-fluoromethyl-2-oxo-pyrrolidin-1-yl)-3-oxo-butyric acid of formula

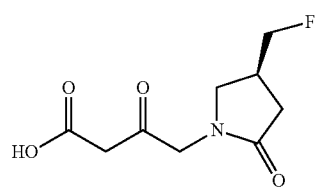

5b or a salt thereof, is a novel compound and thus represents a further embodiment of the invention.

Step f)

Step f) requires the coupling of the ((S)-4-fluoromethyl-2-oxo-pyrrolidin-1-yl)-3-oxo-butyric acid of formula (5b) with an isoquinoline derivative of formula (6) or a salt thereof to form a compound of formula (7a) or a salt thereof and the subsequent ring closing of the compound of formula (7a) with formaldehyde to form the (3S,11bS)-3-(S)-4-fluoromethyl-2-oxo-pyrrolidin-1-yl)-1,3,4,6,7,11b-hexahydro-pyrido[2,1-a]isoquinolin-2-one derivative of formula (7b).

As outlined under step e) the filtrate obtained from step e) and containing ((S)-4-fluoromethyl-2-oxo-pyrrolidin-1-yl)-3-oxo-butyric acid of formula (5b) can be added to the isoquinoline derivative of formula (6) to provide compound of formula (7a) or a salt thereof (depending on the reaction conditions and isolation procedure).

A suitable isoquinoline derivative of formula (6) is the dihydroisoquinoline of formula

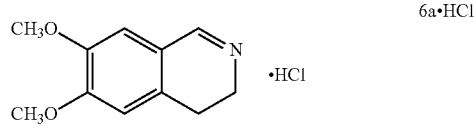

6a·HCl

In this case, preferred conditions involve the reaction of (S)-(4-fluoromethyl-2-oxo-pyrrolidin-1-yl)-3-oxo-butyric acid of formula (5b) with the compound of formula (6a.HCl) in a suitable solvent such as water, lower alcohols or preferably mixtures thereof. The addition of a base is required for the reaction to proceed. Among suitable bases, carboxylic acids salts are preferred, more preferably sodium or potassium acetate, even more preferably sodium acetate. Preferred conditions comprise the use of 0.05 to 1 equivalents, preferably 0.05 to 0.5 equivalents, even more preferably 0.1-0.2 equivalents of sodium acetate in a mixture of ethanol, water and optionally heptane as co-solvent. The product of formula (7a) be conveniently introduced in the next step or can be isolated by direct crystallization (of its hydrochloride salt) or can be isolated by an extractive work-up.

The reaction temperature is as a rule selected between 0° C. and 40° C., preferably between 20° C. and 30° C. The optimal temperature range can vary from substrate to substrate.

The following ring closing is accomplished with aqueous formaldehyde at a temperature of 20° C. to 60° C., preferably 20° C. to 50° C. The optimal temperature range can vary from substrate to substrate. The reaction is performed at a pH between 5 and 7, preferably between 6 and 7.

Separation of the diastereomers and isolation of the specific diastereomer (3S,11bS)-3-((S)-4-fluoromethyl-2-oxo-pyrrolidin-1-yl)-1,3,4,6,7,11b-hexahydro-pyrido[2,1-a]isoquinolin-2-one derivative of formula (7b), preferably of the (3S,11bS)-3-(S)-4-fluoromethyl-2-oxo-pyrrolidin-1-yl)-9,10-dimethoxy-1,3,4,6,7,11b-hexahydro-pyrido[2,1-a]isoquinolin-2-one can happen by silica gel chromatography using a suitable organic solvent such as a mixture of ethylacetate and ethanol or t.-butyl-methylether and ethanol as eluent. Crystallization in a suitable organic solvent for example in dichloromethane/ethanol leads to an even more pure product.

Both the compound of formula

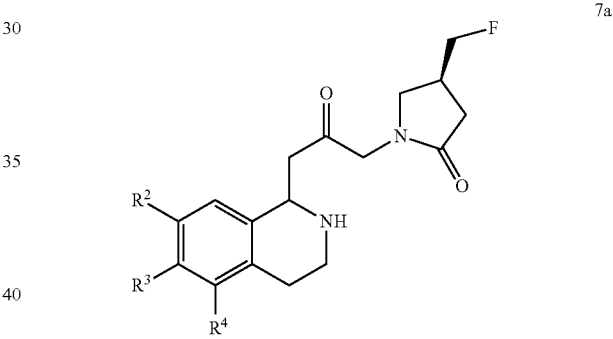

7a wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl, or a salt thereof and the compounds of formula

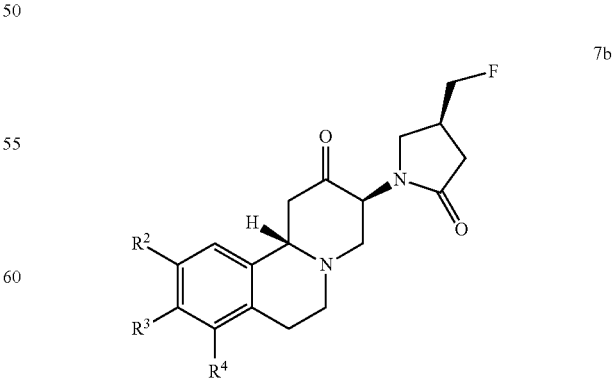

7b wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl, aryl and heterocyclyl, or a salt thereof, are novel compounds and therefore represent a further embodiment of the present invention.

Preferred representatives of the compounds of formula 7a and 7b are those with $R^2$ and $R^3$ being methoxy and $R^4$ being hydrogen. Preferred salt of the compounds of formula 7a and 7b is hydrochloride.

Step g)

Step g) requires the transformation of the (3S,11bS)-3-(S)-4-fluoromethyl-2-oxo-pyrrolidin-1-yl)-1,3,4,6,7,11b-hexahydro-pyrido[2,1-a]isoquinolin-2-one derivative of formula (7b) into the (S)-1-((2S,3S,11bS)-2-N-protected-amino-1,3,4,6,7,11b-hexahydro-2H-pyrido[2,1-a]isoquinolin-3-yl)-4-fluoromethyl-pyrrolidin-2-one of formula (8).

The N-protecting group "Prot" used hereinafter used for the compound of formula (8) may refer to any substituents conventionally used to hinder the reactivity of the amino group. Suitable amino protecting groups are described in Green T., "Protective Groups in Organic Synthesis", Chapter 7, John Wiley and Sons, Inc., 1991, 309-385. The benzyl group was found to be the preferred N-protecting group "Prot".

The exchange of the oxo-group by the N-protected amino group usually follows the principles of a reductive amination (see e.g. E. W. Baxter, A. B. Reitz (2002). "Reductive aminations of carbonyl compounds with borohydride and borane reducing agents." Org. React. (N.Y.) 59: 1-714).

The (3S,11bS)-3-(S)-4-fluoromethyl-2-oxo-pyrrolidin-1-yl)-1,3,4,6,7,11b-hexahydro-pyrido[2,1-a]isoquinolin-2-one derivative of formula (7b), is reacted with the N-protected amine, preferably with benzylamine in the presence of a Ti-organic compound such as titanium tetraisopropoxide in a suitable organic solvent such as tetrahydrofuran at temperatures of 0° C. to 40° C. and by subsequent reduction of the previously formed imine with a common reducing agent such as with sodium borohydride at temperatures of 0° C. to −50° C.

Isolation of (S)-1-((2S,3S,11bS)-2-N-protected-amino-1,3,4,6,7,11b-hexahydro-2H-pyrido[2,1-a]isoquinolin-3-yl)-4-fluoromethyl-pyrrolidin-2-one of formula (8), preferably of the (S)-1-((2S,3S,11bS)-2-N-protected-amino-9,10-dimethoxy-1,3,4,6,7,11b-hexahydro-2H-pyrido[2,1-a]isoquinolin-3-yl)-4-fluoromethyl-pyrrolidin-2-one can happen by filtration over silica gel using a suitable organic solvent, for example a mixture of dichloromethane and methanol as eluent. Evaporation of the solvent and crystallization in a suitable organic solvent, for example in dichloromethane/ethanol leads to an even more pure product.

Step h)

Step h) finally requires the removal of the protecting group Prot in the (S)-1-((2S,3S,11bS)-2-N-protected-amino-1,3,4,6,7,11b-hexahydro-2H-pyrido[2,1-a]isoquinolin-3-yl)-4-fluoromethyl-pyrrolidin-2-one of formula (8) and the formation of the target compound of formula (I).

The removal of the N-protecting group, preferably of the benzyl group can as a rule be accomplished by way of a hydrogenolysis applying conditions which are known to the skilled in the art (see e.g. W. H. Hartung, R. Smirnoff (1953). "Hydrogenolysis of Benzyl Groups Attached to Oxygen, Nitrogen, or Sulfur." Org. React. (N.Y.) 7: 263).

For the preferred debenzylation the hydrogenolysis can as a rule be performed under a hydrogen atmosphere of 1 bar to 10 bar in the presence of a common hydrogenation catalyst such as palladium or platinum on an inert support like charcoal and in a lower alcohol, preferably ethanol as solvent.

The reaction temperature is expediently selected between 0° C. and 60° C., preferably 20° C. to 50° C.

Upon completion of the reaction the reaction mixture is filtered and the filtrate is concentrated to afford the deprotected product.

Subsequent formation of a pharmaceutically acceptable salt of the compound of formula (I) is within the skill of an artisan.

The preferred formation of the dihydrochloride can be accomplished by reacting the deprotected product of formula (I) with a suitable alkanoyl chloride such as with acetyl chloride in a suitable solvent such as in methanol and at reaction temperatures between 0° C. and 30° C. or with HCl in a suitable solvent such as in isopropanol or dioxane.

Most preferred product of formula (I) is the (S)-1-((2S,3S,11bS)-2-amino-9,10-dimethoxy-1,3,4,6,7,11b-hexahydro-2H-pyrido[2,1-a]isoquinolin-3-yl)-4-fluoromethyl-pyrrolidin-2-one dihydrochloride of formula (9)

The following examples shall illustrate the invention without limiting it.

EXAMPLES

Example 1

Synthesis of (R)-4-bromo-3-fluoromethyl-butyric acid methyl ester (2)

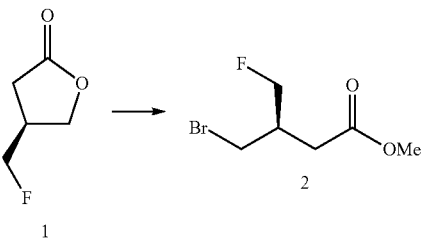 [SMILES: O=C1C[C@H](CF)CO1 ; COC(=O)C[C@H](CF)CBr]

In a 2.5-l four-necked flask equipped with a mechanical stirrer, a reflux condenser, a Pt-100 thermometer, and an argon in/outlet, hydrobromic acid (400 ml, 2.28 mol, 5.7 M in acetic acid) was added to lactone 1 (80 g, 677 mmol). The mixture was heated to 60° C. and stirred for 3 hours to give a clear, yellow solution. Methanol (800 ml) was added over 10 minutes under ice cooling, keeping the temperature below 30° C. The resulting mixture was stirred at ambient temperature for 19 hours and then concentrated under reduced pressure at 40° C. The residue was diluted with toluene (400 ml) and saturated aqueous sodium bicarbonate (1000 ml) was slowly added under $CO_2$ evolution. The phases were separated and the organic layer was washed with water (200 ml), dried over anhydrous $Na_2SO_4$, filtered, and concentrated under reduced pressure at 40° C. to give 139 g of the crude product as yellow oil. The crude product was purified by vacuum distillation (62-65° C., 0.9 mbar) to give ester 2 (111.3 g, 77% yield) of as a colorless oil.

MS: m/e 213 (M+H)$^+$.

Example 2

Synthesis of (S)-4-(benzyl-ethoxycarbonylmethyl-amino)-3-fluoromethyl-butyric acid methyl ester (3)

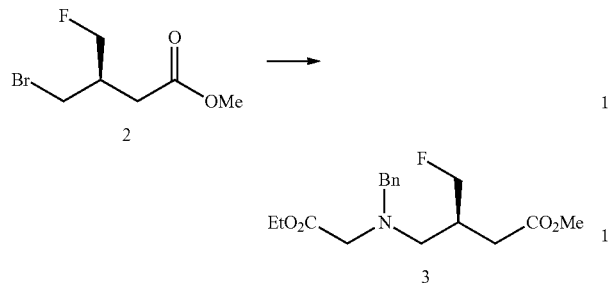

In a 2.5-l four-necked flask equipped with a mechanical stirrer, a reflux condenser, a Pt-100 thermometer, and an argon in/outlet, bromide 2 (110 g, 519 mmol) was dissolved in acetonitrile (880 ml). To this solution was added N-benzylglycine ethyl ester (256 g, 1.30 mol) and the reaction mixture was refluxed for 71 hours, slowly turning dark red during this time. After cooling to room temperature, the mixture was concentrated under reduced pressure. The dark red oil was filtered over silica gel (800 g) using EtOAc:heptane 1:9 as eluent, giving the crude title compound 3 (169 g) as yellow oil which was used without further purification.

MS: m/e 326 $(M+H)^+$.

Example 3

Synthesis of ((S)-4-fluoromethyl-2-oxo-pyrrolidin-1-yl)-acetic acid ethyl ester (4)

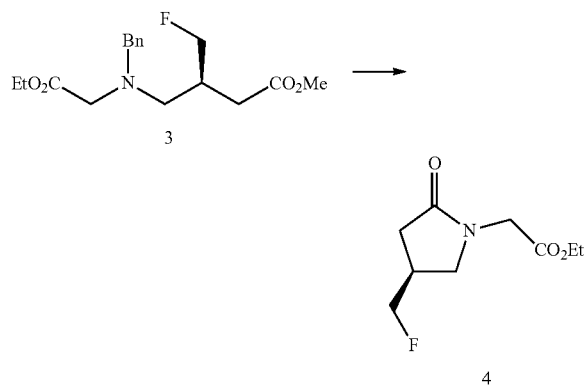

In a 5-l reactor, ester 3 (148 g, 455 mmol) is dissolved in ethanol (500 ml) and a suspension of palladium on charcoal (13.8 g, 10 wt % Pd) in ethanol (40 ml) is added in one portion. The mixture is stirred for 2 hours at 20° C. under hydrogen atmosphere (1.1 bar). The reaction mixture is filtered and the filter cake washed with ethanol. The filtrate is concentrated under reduced pressure at 40° C. to a volume of ca. 500 ml and the solution obtained is stirred at reflux temperature for 6 hours. After cooling to ambient temperature, the solvent is removed under reduced pressure at 40° C. The crude product (92.0 g) is fractionally distilled under reduced pressure (0.75 mbar, 134-139° C.) to give ester 5 (75.5 g, 81% yield) as a colorless oil.

MS: m/e 204 $(M+H)^+$, 130, 158.

Example 4

Synthesis of 4-((S)-4-fluoromethyl-2-oxo-pyrrolidin-1-yl)-3-oxo-butyric acid benzyl ester (5)

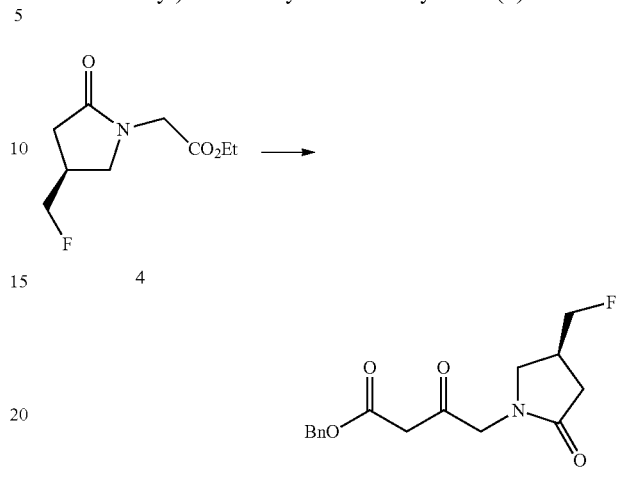

In a 2.5-l four-necked flask equipped with a mechanical stirrer, a Pt-100 thermometer, an addition funnel, and an argon in/outlet, diisopropylamine (112 ml, 792 mmol) was dissolved in 960 ml THF and the mixture was cooled to −30° C. n-Butyllithium (507 ml, 787 mmol, 1.55 m in hexanes) was added dropwise over 35 minutes and the clear solution was stirred for 30 minutes at −25° C. after the end of the addition. After further cooling to −70° C., benzyl acetate (114 ml, 794 mmol) was added dropwise over 35 minutes and the yellow solution was stirred for another 1.5 hours. A solution of ethyl ester 4 (80.0 g, 394 mmol) in THF (40 ml) was added over 1 hour at −70° C. at the mixture was allowed to warm to −25° C. over 90 minutes after the end of the addition.

The reaction was quenched by addition of the reaction mixture to 1.0 m aqueous hydrochloric acid (2000 ml). The organic solvents were removed by evaporation under reduced pressure at 40° C. and the residual aqueous layer was extracted with dichloromethane (3×970 ml). The combined organic layers were dried over anhydrous $Na_2SO_4$, filtered, and concentrated under reduced pressure at 40° C., giving an orange oil (176.5 g). The crude product was purified by silica gel chromatography (1.75 kg silica gel), eluting with EtOAc:heptane 3:1. Ester 5 (109 g, 90% yield) was isolated as a yellowish oil.

MS: m/e 308 $(M+H)^+$, 325, 330 $(M+Na)^+$.

Example 5

Synthesis of 4-((S)-4-fluoromethyl-2-oxo-pyrrolidin-1-yl)-3-oxo-butyric acid benzyl acid (5b)

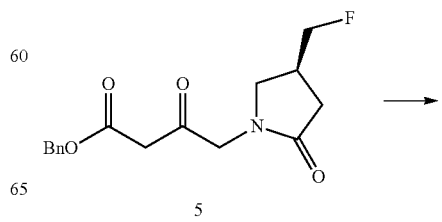

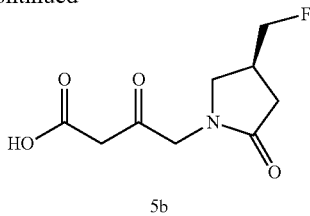

In a 10-ml two-necked flask equipped with a magnetic stir bar, benzyl ester 5 (150 mg, 0.488 mmol) was dissolved in methanol (1.5 ml) and palladium on charcoal (10.0 mg, 10 wt % Pd) was added. The mixture was stirred for 2 hours under a hydrogen atmosphere (1 bar) and then filtered, washing the filter cake with ethanol (1.6 ml). The volatiles were removed under reduced pressure at ambient temperature and the crude keto ester 5b (105 mg, 99% yield) was obtained as a clear, colorless oil.

MS: m/e 218 (M+H)$^+$.

Example 6

Synthesis of (3S,11bS)-3-(S)-4-fluoromethyl-2-oxo-pyrrolidin-1-yl)-9,10-dimethoxy-1,3,4,6,7,11b-hexahydro-pyrido[2,1-a]isoquinolin-2-one (7)

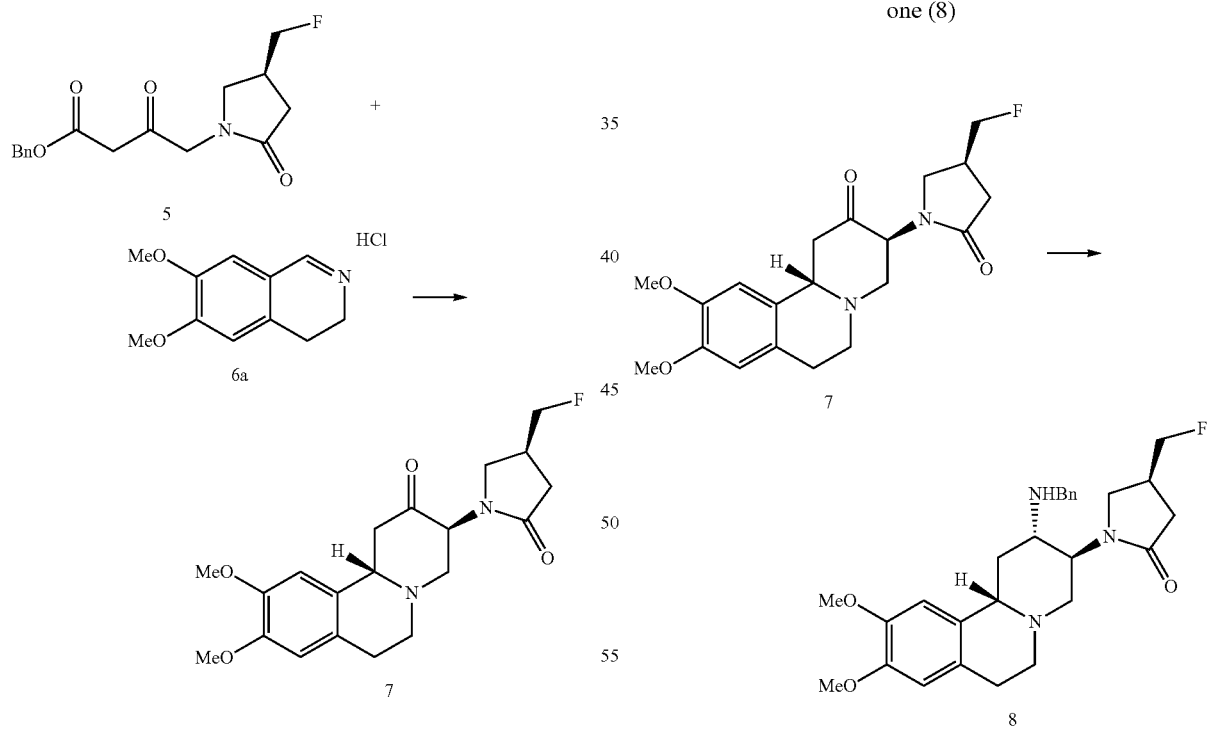

In a 350-ml four-necked flask equipped with a gas-injection stirrer and a Pt-100 thermometer, benzyl ester 5 (16.19 g, 52.7 mmol) was dissolved in ethanol (134 ml) and palladium on charcoal (1.07 g, 10 wt % Pd) was added. The mixture was stirred for 80 minutes under a hydrogen atmosphere (1 bar) and then filtered, washing the filter cake with ethanol (20 ml).

The yellowish filtrate was added over 10 minutes to a mixture of dihydroisoquinoline 6 (12.0 g, 52.7 mmol), sodium acetate (432 mg, 5.24 mmol), and water (3.7 ml) in ethanol (56 ml) under evolution of $CO_2$, the temperature being maintained between 20° C. and 23° C. using a cooling bath. After the end of the addition, stirring was maintained for 4 hours, leading to an off-white suspension.

Sodium acetate (3.89 g, 47.2 mmol) (pH of reaction mixture ca. 7) and aqueous formaldehyde solution (4.5 ml, 60.3 mmol, 36.5% in $H_2O$) were added and the resulting mixture was stirred at 40° C. for 17 hours. The off-white suspension is slowly cooled to 0° C. over 3 hours and stirred at this temperature for 6 hours. The solids are filtered off and washed with ethanol (8 ml).

The solid residue is purified by chromatography over silica gel (650 g), using EtOAc:EtOH 9:1 as eluent. After evaporation of the solvent, the purified product was dissolved in dichloromethane (40 ml) and ethanol (23 ml) was added. Upon evaporation of dichloromethane under reduced pressure at 40° C., crystallization occurred. The suspension was stirred at ambient temperature for 3 hours. The crystals were filtered off, washed with ethanol (6 ml) and dried under reduced pressure (10 mbar, 50° C.) for 24 hours, giving ketone 7 (5.18 g, 26% yield) as white crystals.

Melting point (Mp)=134° C.

MS: m/e 377 (M+H)$^+$, 399 (M+Na)$^+$.

Example 7

Synthesis of (S)-1-((2S,3S,11bS)-2-benzylamino-9,10-dimethoxy-1,3,4,6,7,11b-hexahydro-2H-pyrido[2,1-a]isoquinolin-3-yl)-4-fluoromethyl-pyrrolidin-2-one (8)

In a 350-ml four-necked flask equipped with a mechanical stirrer, a Pt-100 thermometer, an argon in/outlet and a rubber septum, ketone 7 (10 g, 26.6 mmol) was suspended in THF (150 ml). Titanium tetraisopropoxide (15.7 ml, 53.1 mmol) and benzyl amine (5.9 ml, 53.1 mmol) were added to give an orange solution which was stirred at room temperature for 1 hour. Sodium borohydride (1.57 g, 39.9 mmol) was added and, after cooling the mixture to −30° C., ethanol (20 ml) was added dropwise over 6 minutes. The reaction mixture is stirred at −30° C. for 15 minutes and then allowed to slowly warm to 0° C. over 45 minutes. After 100 minutes at 0° C., the solvent is removed by evaporation under reduced pressure to give a solid residue, which is suspended in dichloromethane (100 ml) and stirred at room temperature for 15 minutes. After filtration, the dichloromethane solution is filtered over a plug of silica gel (150 g), using $CH_2Cl_2$:MeOH 19:1 as eluent. Evaporation of the volatiles under reduced pressure affords a white solid (12.6 g), which is dissolved in dichloromethane (100 ml). Ethanol (200 ml) is added and dichloromethane is evaporated under reduced pressure at 40° C. under stirring, leading to crystallization. After stirring for 15 hours at ambient temperature, the crystals are filtered off, washed with ethanol (5 ml) and dried under reduced pressure (10 mbar, 50° C.) to give amine 8 (8.61 g, 69% yield) as white crystals.

Mp=192° C. (decomp.)
MS: m/e 468 (M+H)+.

Example 7

Synthesis of (S)-1-((2S,3S,11bS)-2-amino-9,10-dimethoxy-1,3,4,6,7,11b-hexahydro-2H-pyrido[2,1-a]isoquinolin-3-yl)-4-fluoromethyl-pyrrolidin-2-one dihydrochloride (9)

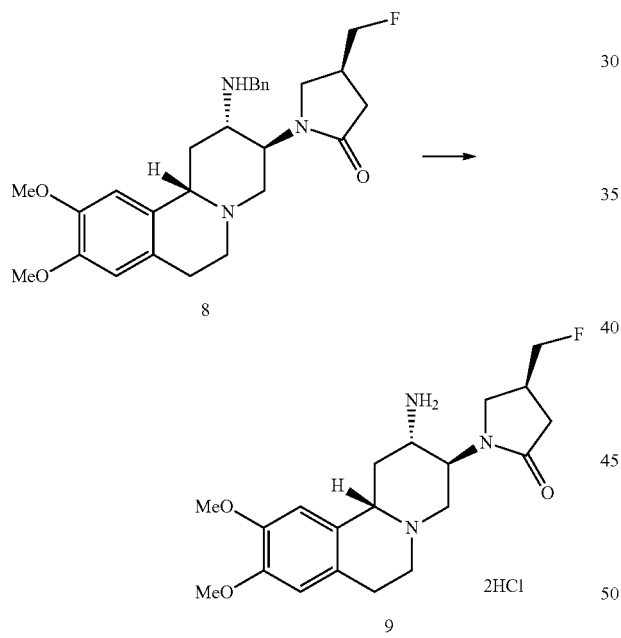

In a 1.5-l glass autoclave, benzyl amine 8 (8.5 g, 18.2 mmol) was dissolved in methanol (300 ml) and palladium on charcoal (1.68 g, 10 wt % Pd) was added under argon. The reactor is sealed and flashed with hydrogen. The mixture is hydrogenated at 40° C. under a pressure of 4 bar. The reaction mixture is filtered, and the filter cake is washed with methanol.

The filtrate is concentrated under reduced pressure at 40° C. to afford 6.65 g (97% crude yield) of the debenzylated product as an off-white solid.

Acetyl chloride (5.1 ml) is added carefully under ice-cooling to methanol (22.7 ml), keeping the temperature below 17° C. This solution is added at room temperature over 40 minutes to a solution of the crude product in methanol (50 ml), whereupon crystallization occurs. After completion of the addition, stirring is maintained for 2 hours. The solid is recovered by filtration, washed with methanol (7 ml), and dried under reduced pressure (10 mbar, 50° C.). Dihydrochloride 9 (7.13 g, 87% yield) is isolated as white crystals.

MS: m/e 378 (M−2HCl+H)+, 400 (M−2HCl+Na)+.

The invention claimed is:
1. A process for the preparation of pyrido[2,1-a]isoquinoline derivatives of the formula

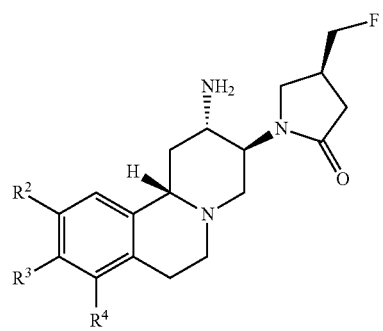

wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl and aryl,
and of pharmaceutically acceptable salts thereof,
comprising one or more of the following steps
a) ring opening of (S)-4-fluoromethyl-dihydro-furan-2-one of the formula

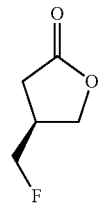

and subsequent esterification to provide the (R)-4-bromo-3-fluoromethyl-butyric acid ester of the formula

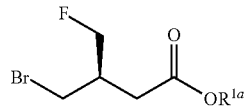

wherein $R^{1a}$ is lower alkyl;
b) converting the (R)-4-bromo-3-fluoromethyl-butyric acid ester of the formula (2) with an N-protected glycine alkylester into a N-protected —(S)-4-(alkoxycarbonyl-methyl-amino)-3-fluoromethyl-butyric acid ester of formula

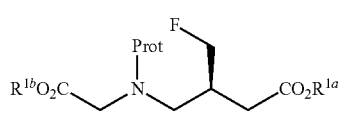

wherein $R^{1a}$ and $R^{1b}$ are lower alkyl and Prot is an amino protecting group;

c) deprotection of the N-protected —(S)-4-(alkoxycarbonylmethyl-amino)-3-fluoromethyl-butyric acid ester of formula (3) and subsequent ring closure to form the ((S)-4-fluoromethyl-2-oxo-pyrrolidin-1-yl)-acetic acid ester of formula

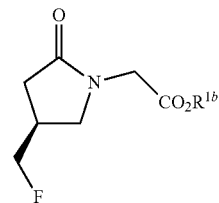

wherein $R^{1b}$ is lower alkyl;

d) converting the ((S)-4-fluoromethyl-2-oxo-pyrrolidin-1-yl)-acetic acid ester of formula (4) into the ((S)-4-fluoromethyl-2-oxo-pyrrolidin-1-yl)-3-oxo-butyric acid ester of formula

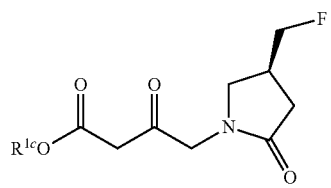

wherein $R^{1c}$ is a protecting group, or a salt thereof;

e) transforming the ((S)-4-fluoromethyl-2-oxo-pyrrolidin-1-yl)-3-oxo-butyric acid ester of formula (5a) into the ((S)-4-fluoromethyl-2-oxo-pyrrolidin-1-yl)-3-oxo-butyric acid of formula

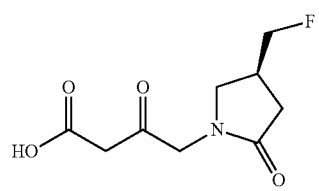

or a salt thereof;

f) coupling the ((S)-4-fluoromethyl-2-oxo-pyrrolidin-1-yl)-3-oxo-butyric acid of formula (5b) with an isoquinoline derivative of formula

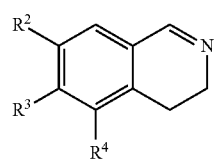

wherein $R^2$, $R^3$ and $R^4$ are as above, or a salt thereof to form a compound of formula

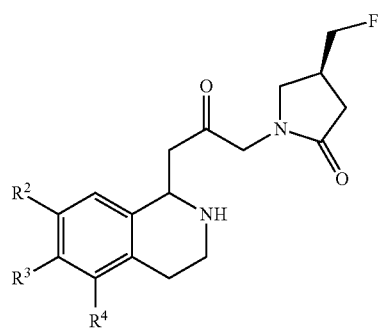

wherein $R^2$, $R^3$ and $R^4$ are as above or of a salt thereof, subsequently ring closing the compound of formula (7a) with formaldehyde to form the (3S,11bS)-3-((S)-4-fluoromethyl-2-oxo-pyrrolidin-1-yl)-1,3,4,6,7,11b-hexahydro-pyrido[2,1-a]isoquinolin-2-one derivative of formula

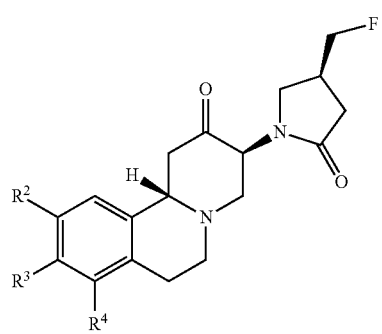

wherein $R^2$, $R^3$ and $R^4$ are as above, or a salt thereof;

g) transforming the (3S,11bS)-3-((S)-4-fluoromethyl-2-oxo-pyrrolidin-1-yl)-1,3,4,6,7,11b-hexahydro-pyrido[2,1-a]isoquinolin-2-one derivative of formula (7b) into the (S)-1-((2S,3S,11bS)-2-N-protected-amino-1,3,4,6,7,11b-hexahydro-2H-pyrido[2,1-a] isoquinolin-3-yl)-4-fluoromethyl-pyrrolidin-2-one of formula

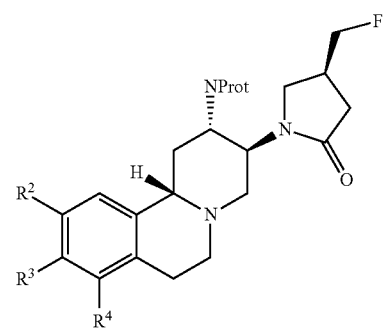

wherein $R^2$, $R^3$ and $R^4$ and Prot are as above, or a salt thereof;

h) removing the protecting group Prot in the (S)-1-((2S,3S,11bS)-2-N-protected-amino-1,3,4,6,7,11b-hexahydro-2H-pyrido[2,1-a]isoquinolin-3-yl)-4-fluoromethyl-pyrrolidin-2-one of formula (8).

2. The process according to claim 1, characterized in that the pyrido[2,1-a]isoquinoline derivative of the formula I is

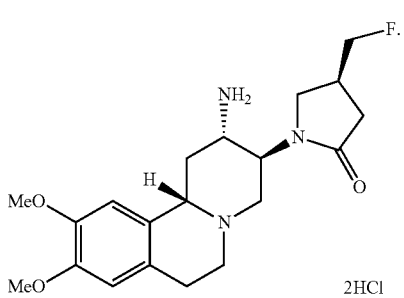

in the presence of a base.

3. The process according to claim 1, characterized in that the formation of the (R)-4-bromo-3-fluoromethyl-butyric acid ester of the formula (2) in step a) is performed with hydrobromic acid at a reaction temperature of 20° C. to 100° C.

4. The process according to claim 1, characterized in that the subsequent esterification in step a) is performed in a lower alcohol.

5. The process according to claim 1, characterized in that the N-protected glycine alkylester used for the formation of N-protected-(S)-4-(alkoxycarbonylmethyl-amino)-3-fluoromethyl-butyric acid ester of formula (3) in step b) is the N-benzyl glycine ethylester.

6. The process according to claim 1, characterized in that the conversion in step b) is performed in a polar aprotic solvent at a temperature of 60° C. to the reflux temperature of the solvent.

7. The process according to claim 1, characterized in that the formation of the ((S)-4-fluoromethyl-2-oxo-pyrrolidin-1-yl)-acetic acid ester of formula (4) in step c) is a hydrogenolysis to remove the N-protecting group under a hydrogen atmosphere of 1 bar to 10 bar in the presence of a hydrogenation catalyst followed by a subsequent ring closing reaction at increased temperature.

8. The process according to claim 1, characterized in that the formation of ((S)-4-fluoromethyl-2-oxo-pyrrolidin-1-yl)-3-oxo-butyric acid ester of formula (5a) in step d) is performed via condensation of an enolate in situ formed by deprotonating an acetic acid ester of the formula

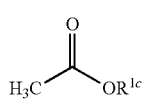

wherein $R1^c$ is a protecting group in the presence of a non nucleophilic strong organic base with the ((S)-4-fluoromethyl-2-oxo-pyrrolidin-1-yl)-acetic acid ester of formula (4) at a temperature of −50° C. to −100° C. in an organic solvent.

9. The process according to claim 1, characterized in that the formation of the ((S)-4-fluoromethyl-2-oxo-pyrrolidin-1-yl)-3-oxo-butyric acid of formula (5b) in step e) is performed by way of a hydrogenolysis to remove the protecting group $R^{1c}$ under a hydrogen atmosphere of 1 bar to 10 bar in the presence of a hydrogenation catalyst.

10. The process according to claim 1, characterized in that the ((S)-4-fluoromethyl-2-oxo-pyrrolidin-1-yl)-3-oxo-butyric acid of formula (5b) is not isolated, but without isolation transferred to the reaction step f).

11. The process according to claim 1, characterized in that the formation of the compound of the formula (7a) in step f) is performed with the isoquinoline derivative of formula 12. The process according to claim 1, characterized in that the formation of (3S,11bS)-3-((S)-4-fluoromethyl-2-oxo-pyrrolidin-1-yl)-1,3,4,6,7,11b-hexahydro-pyrido[2,1-a]isoquinolin-2-one derivative of formula (7b) in step f) is performed with aqueous formaldehyde at a temperature of 20° C. to 60° C.

13. The process according to claim 1, characterized in that the formation of the (S)-1-((2S,3S,11bS)-2-N-protected-amino-1,3,4,6,7,11b-hexahydro-2H-pyrido[2,1-a] isoquinolin-3-yl)-4-fluoromethyl-pyrrolidin-2-one of formula (8) in step g) is performed by reductive amination of the (3S,11bS)-3-((S)-4-fluoromethyl-2-oxo-pyrrolidin-1-yl)-1,3,4,6,7,11b-hexahydro-pyrido[2,1-a] isoquinolin-2-one derivative of formula (7b).

14. The process according to claim 1, characterized in that the reductive amination is performed by reacting the (3S,11bS)-3-((S)-4-fluoromethyl-2-oxo-pyrrolidin-1-yl)-1,3,4,6,7,11b-hexahydro-pyrido[2,1-a]isoquinolin-2-one derivative of formula (7b) with benzylamine in the presence of Ti-organic compound and by reducing the formed imine with a reducing agent.

15. The process according to claim 1, characterized in that the removal of the protecting group Prot of the (S)-1-((2S,3S,11bS)-2-N-protected-amino-1,3,4,6,7,11b-hexahydro-2H-pyrido[2,1-a]isoquinolin-3-yl)-4-fluoromethyl-pyrrolidin-2-one of formula (8) and the formation of the pyrido[2,1-a]isoquinoline derivative of the formula (I) in step h) is performed by way of a hydrogenolysis under a hydrogen atmosphere of 1 bar to 10 bar in the presence of a hydrogenation catalyst.

16. A compound of formula 7a:

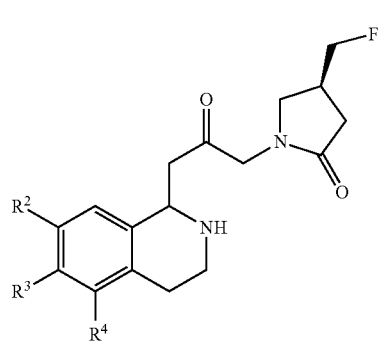

wherein $R^2$, $R^3$ and $R^4$ are each independently selected from the group consisting of hydrogen, halogen, hydroxy, lower alkyl, lower alkoxy and lower alkenyl, wherein lower alkyl, lower alkoxy and lower alkenyl may optionally be substituted by a group selected from lower alkoxycarbonyl and aryl, or of a salt thereof.

* * * * *